(12) United States Patent
Cuevas et al.

(10) Patent No.: US 10,272,175 B2
(45) Date of Patent: Apr. 30, 2019

(54) FOAMS FOR OXYGEN DELIVERY TO WOUNDS

(71) Applicant: Avent, Inc., Alpharetta, GA (US)

(72) Inventors: Brian J. Cuevas, Cumming, GA (US); Sophie Truc Lam, Beaverton, OR (US); Nathan G. Bonn-Savage, Amity, OR (US); Ramanathan S. Lalgudi, Westerville, OH (US); Melissa S. Roshon, Hilliard, OH (US); Robert Jonathan Cain, Lewis Center, OH (US)

(73) Assignee: Avent, Inc., Alpharetta, GA (US)

( * ) Notice: Subject to any disclaimer, the term of this patent is extended or adjusted under 35 U.S.C. 154(b) by 30 days.

(21) Appl. No.: 15/033,752

(22) PCT Filed: Nov. 26, 2014

(86) PCT No.: PCT/US2014/067530
§ 371 (c)(1),
(2) Date: May 2, 2016

(87) PCT Pub. No.: WO2015/081151
PCT Pub. Date: Jun. 4, 2015

(65) Prior Publication Data
US 2016/0279285 A1 Sep. 29, 2016

Related U.S. Application Data

(60) Provisional application No. 61/909,039, filed on Nov. 26, 2013.

(51) Int. Cl.
| | |
|---|---|
| A61L 15/00 | (2006.01) |
| A61L 15/20 | (2006.01) |
| A61L 26/00 | (2006.01) |
| A61L 15/18 | (2006.01) |
| A61L 15/26 | (2006.01) |
| A61L 15/42 | (2006.01) |
| A61L 15/44 | (2006.01) |
| A61L 15/60 | (2006.01) |
| A61L 15/64 | (2006.01) |

(52) U.S. Cl.
CPC .......... *A61L 26/0066* (2013.01); *A61L 15/18* (2013.01); *A61L 15/26* (2013.01); *A61L 15/425* (2013.01); *A61L 15/44* (2013.01); *A61L 15/60* (2013.01); *A61L 15/64* (2013.01); *A61L 26/0004* (2013.01); *A61L 26/008* (2013.01); *A61L 26/009* (2013.01); *A61L 26/0019* (2013.01); *A61L 26/0085* (2013.01); *A61L 2300/11* (2013.01); *A61L 2300/412* (2013.01)

(58) Field of Classification Search
CPC combination set(s) only.
See application file for complete search history.

(56) References Cited

U.S. PATENT DOCUMENTS

| | | | |
|---|---|---|---|
| 5,736,582 A | 4/1998 | Devillez | |
| 7,014,630 B2 | 3/2006 | Rosati | |
| 7,160,553 B2 | 1/2007 | Gibbins et al. | |
| 7,762,045 B2 | 7/2010 | Rosati | |
| 7,813,807 B2 | 10/2010 | Franklin | |
| 8,075,537 B2 | 12/2011 | Franklin et al. | |
| 8,166,731 B2 | 5/2012 | Rosati | |
| 8,900,209 B2 | 12/2014 | Rosati | |
| 8,974,776 B2 * | 3/2015 | Stopek | A61K 9/0024 424/85.2 |
| 8,999,377 B2 | 4/2015 | Rolfes et al. | |
| 2005/0251084 A1 | 11/2005 | Rosati | |
| 2006/0121101 A1 | 6/2006 | Ladizinsky | |
| 2006/0200100 A1 | 9/2006 | Rosati | |
| 2008/0021373 A1 | 1/2008 | Rosati | |
| 2010/0038280 A1 | 2/2010 | Franklin et al. | |
| 2010/0041998 A1 | 2/2010 | Postel | |
| 2010/0063462 A1 | 3/2010 | Postel et al. | |
| 2010/0087946 A1 | 4/2010 | Postel et al. | |
| 2011/0257610 A1 | 10/2011 | Franklin | |
| 2011/0257617 A1 | 10/2011 | Franklin | |
| 2011/0282259 A1 | 11/2011 | Postel et al. | |
| 2012/0059301 A1 | 3/2012 | Franklin | |
| 2012/0136081 A1 * | 5/2012 | Blume | A61L 15/42 521/78 |
| 2012/0265124 A1 | 10/2012 | Karandikar et al. | |
| 2013/0296630 A1 | 11/2013 | Franklin | |

FOREIGN PATENT DOCUMENTS

WO WO 97/15287 A1 5/1997

OTHER PUBLICATIONS

Data Sheet for Desmodur E 305 from Bayer MaterialScience. (Year: 2013).*
International Search Report and Written Opinion for PCT/US2014/067530, dated Feb. 10, 2015, 12 pages.

* cited by examiner

*Primary Examiner* — Kara B Boyle
(74) *Attorney, Agent, or Firm* — Dority & Manning, P.A.

(57) ABSTRACT

There is provided a composition comprising covalently linked segments of for example, polycaprolactone and polyethylene glycol that are linked by a cross-linker. Such a composition foams in the presence of a catalyst and a solution containing an oxygen forming chemical like hydrogen peroxide. The foamed composition retains oxygen for delivery to, for example, a wound, where it aids in healing.

5 Claims, 3 Drawing Sheets

| Polymers | Structures | |
|---|---|---|
| Poly(ethylene glycol)-block-poly(ε-caprolactone) | 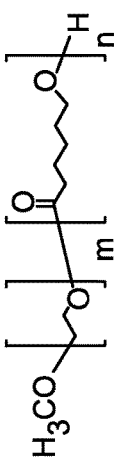 | FIG. 1 |
| Poly(ethylene glycol)-block-polylactide | 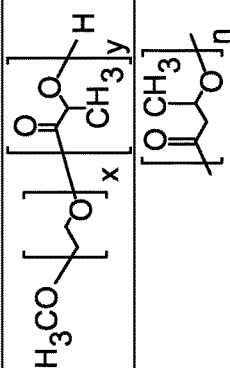 | FIG. 2 |
| Poly3-hydroxybutyric acid | 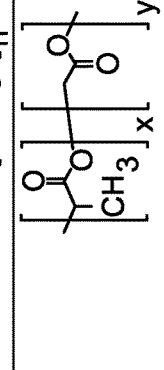 | FIG. 3 |
| Poly(D,L-lactide-co-glycolide) | 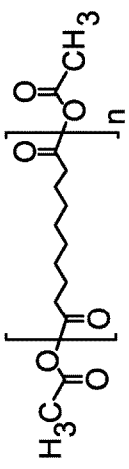 | FIG. 4 |
| Poly(sebacic acid) | 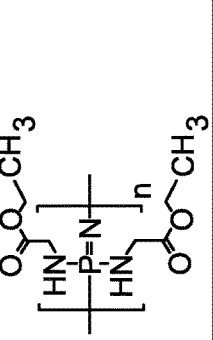 | FIG. 5 |
| Polyphosphazenes | 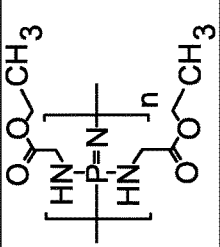 | FIG. 6 |

| | | | |
|---|---|---|---|
| I | Caprolactone Diol<br>PERSTORP CAPA 2054<br>PERSTORP CAPA 2205 | 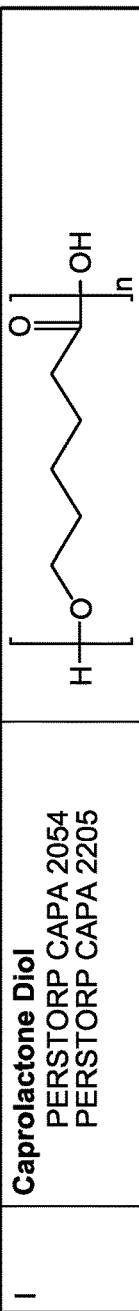 | FIG. 7 |
| II | OH Functional Prepolymer<br>Battelle (idealized structure) | 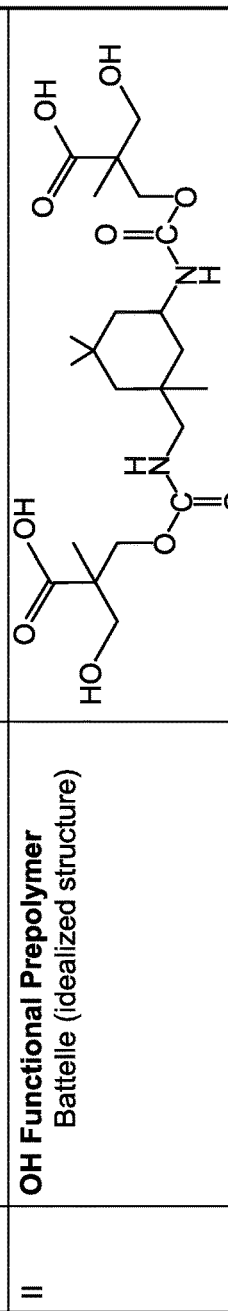 | FIG. 8 |
| III | NCO Prepolymer | 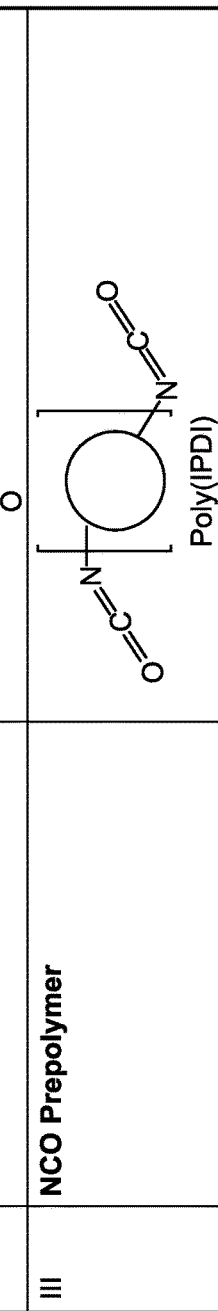 | FIG. 9 |
| IV | Caprolactone Triol Crosslinker<br>PERSTORP CAPA 3031 | 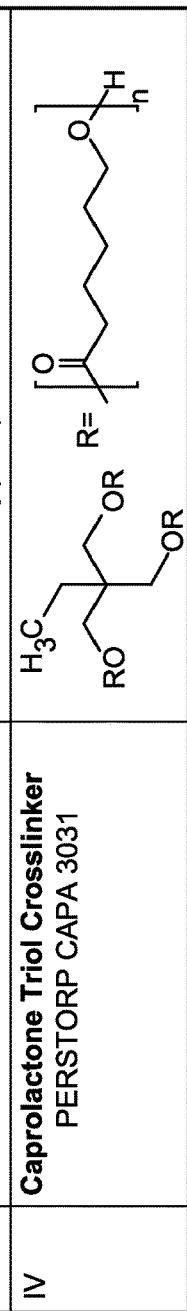 | FIG. 10 |

| | | |
|---|---|---|
| — | Poly (lactide diol) | 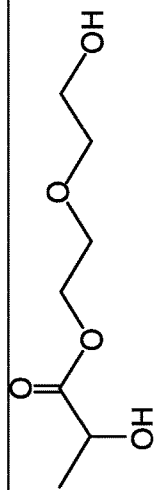 FIG. 11 |
| — | Poly (ethylene glycol)<br>Commercially Available<br>Aldrich 600MW<br>Aldrich 2000MW | 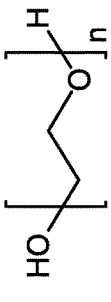 FIG. 12 |
| — | Trimethylene Carbonate<br>(1,3-Dioxan-2-one) | 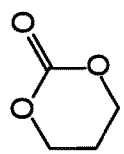 FIG. 13 |
| = | Caprolactone | 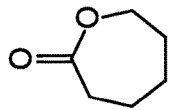 FIG. 14 |
| — | Hydroxybutyric Acid Glycerol Ester | 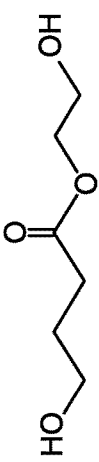 FIG. 15 |

FOAMS FOR OXYGEN DELIVERY TO WOUNDS

Related Applications

The present application is the national stage entry of International Patent Application No. PCT/US2014/067530 having a filing date of Nov. 26, 2014, which claims priority to U.S. Provisional Application Ser. No. 61/909,039, filed on Nov. 26, 2013, both of which are incorporated herein in their entirety by reference thereto.

BACKGROUND OF THE INVENTION

The present disclosure relates to the provision of oxygen for use in wound healing.

The lack of oxygen, i.e. hypoxia, is commonly experienced by people in their extremities as they get older due to poor blood circulation as well as by those with conditions such as diabetes. Studies have also shown below normal, low oxygen tension in the skins of older people. This often leads to poor skin health and an excessive presence of visible conditions such as wrinkles, dryness and lower skin elasticity. Over the years, cosmetic manufacturers have introduced skin formulations with a large variety of ingredients such as emollients, exfoliators, moisturizers etc., to retard these age related effects and improve and maintain skin health. Attacking the problem of low oxygen directly has not been generally practiced.

In addition to the normal decrease in oxygen delivery to the skin which can have beneficial results when reversed, oxygen applied to wounds as, for example, a dressing containing oxygen, can speed healing. The delivery of oxygen to the skin and wounds for common use is a technological challenge, since oxygen is quite reactive and unstable. High concentrations of oxygen could not be provided for home use because of this instability. Oxygen can, however, be provided in the form of a peroxide and a peroxide decomposition catalyst per U.S. Patent Application Publication No. 2006/0121101 to Ladizinsky. This publication provides such a treatment for intact skin through the use of a dressing that is applied to an area of the skin. The dressing generally has a rupturable reservoir containing an aqueous hydrogen peroxide composition and a hydrogel layer having a peroxide decomposition catalyst. Unfortunately the catalytic decomposition of hydrogen peroxide to oxygen is quite rapid and so the dressing has a layer that is impermeable to oxygen on the outside so that the oxygen is held against the skin for the maximum time possible. While this dressing is useful for small areas of the skin, it should be clear that it is unworkable for large areas or irregularly shaped areas of skin.

Alternatively, U.S. Pat. No. 5,736,582 to Devillez proposes the use of hydrogen peroxide in the place of benzoyl peroxide in skin treatment compositions that also contain solvents for hydrogen peroxide. This allows the hydrogen peroxide to stay below a level that will damage the skin and to stay in solution in greater concentrations. A solvent such as dimethyl isosorbide along with water is taught as being effective. No peroxide decomposition catalyst is present. Unfortunately, no data on oxygen concentration or generation are given, nor is the time required for oxygen liberation. While this method appears to be an advance over non-oxygen containing compositions, the lack of data makes it difficult to make objective judgments on the overall effectiveness of this approach. Given the concentrations of peroxide, however, it is doubtful that significant volumes of oxygen were generated.

There is a need for an easy-to-use way of applying oxygen to wounds to accelerate healing. Such a method and/or product should have relatively few components and be intuitive to use, without the need for special dressings or other awkward requirements. A product that may be used in a manner similar to known products would be most readily accepted by the consumer.

SUMMARY

The problem discussed above has found a solution to a large degree in the present disclosure, which describes the use of a composition of polymeric materials that can foam and contains or generates oxygen. The foam is desirably biodegradable with a weight loss of greater than 10 weight percent in 10 days, desirably without the release of any toxic products from the biodegradation.

The composition has covalently linked segments of a biodegradable polymer such as but not limited to polycaprolactone, polylactide, polybutylene succinate, polyhydroxy alkanote and mixtures thereof and a polymer hydrogel such as but not limited to polyethylene glycol, polyhydroxyethylmethacrylate, polyacrylamide, polyacrylic acid, carboxylmethyl cellulose, guar gum and mixtures thereof. It is made by the mixing of the two pre-polymers and a cross-linking agent that connects the biodegradable polymer matrix and the hydrogel polymer matrix. One pre-polymer may be an isocyanate terminated polycaprolactone (CAPA) and the second pre-polymer may be a hydroxyl terminated polyethylene glycol (PEG). The cross-linker may be a commercially available aliphatic isocyanate cross-linker.

The composition forms an oxygen containing foam upon exposure to an oxygen forming chemical, e.g., a solution containing hydrogen peroxide and a catalyst. The catalyst may be chosen from alkali and alkaline earth metals and transition metal oxides. The oxygen containing foam retains oxygen for delivery to, for example, a wound, where it aids in healing.

BRIEF DESCRIPTION OF THE DRAWINGS

FIG. 1 is a representation of the formula of poly(ethylene glycol)-block-poly (ε-caprolactone).

FIG. 2 is a representation of the formula of poly(ethylene glycol)-block-polylactide.

FIG. 3 is a representation of the formula of poly3-hydroxybutyric acid.

FIG. 4 is a representation of the formula of poly(D,L-lactide-co-glycolide).

FIG. 5 is a representation of the formula of poly(sebacic acid).

FIG. 6 is a representation of the formula of polyphosphazenes.

FIG. 7 is a representation of the formula of caprolactone diol.

FIG. 8 is a representation of an idealized structural formula of OH Functional prepolymer.

FIG. 9 is a representation of the formula of NCO prepolymer.

FIG. 10 is a representation of the formula of caprolactone Triol cross-linker.

FIG. 11 is a representation of the formula of poly(lactide diol).

FIG. 12 is a representation of the formula of poly(ethylene glycol).

FIG. 13 is a representation of the formula of trimethylene carbonate(1,3-Dioxan-2-one).

FIG. 14 is a representation of the formula of caprolactone.

FIG. 15 is a representation of the formula of hydroxybutyric acid glycerol ester.

DETAILED DESCRIPTION

Reference will now be made in detail to one or more embodiments of the invention, examples of the invention, examples of which are illustrated in the drawings. Each example and embodiment is provided by way of explanation of the invention, and is not meant as a limitation of the invention. For example, features illustrated or described as part of one embodiment may be used with another embodiment to yield still a further embodiment. It is intended that the invention include these and other modifications and variations as coming within the scope and spirit of the invention.

We have synthesized six individual polymer segments and covalently linked them to form the desired polymer matrix. Biodegradation assays confirmed the polyethylene glycol based matrix and the polycaprolactone based matrix each met the biodegradation goal. The oxygen concentration analysis suggested the foam had 25 ppm of oxygen delivered within 24 hours.

We have made improvements towards foam forming ability to the polymer matrix by adding hydrocolloids which includes but not limited to guar gum and polyvinyl pyrrolidone. The oxygen concentration analysis of the foam obtained from the improved foam forming formulations was also found to contain 25 ppm of oxygen.

Based on our detailed understanding of the structure-activity relationship reported in the literature, we selected the top biodegradable polymer segments that could possibly meet the biodegradability and biocompatibility criteria for the polymer matrix. These are poly(ethylene glycol)-block-poly(ε-caprolactone), with a structure shown in FIG. 1; poly(ethylene glycol)-block-polylactide, FIG. 2; poly3-hydroxybutyric acid, FIG. 3; poly(D,L-lactide-co-glycolide) FIG. 4; poly(sebacic acid), FIG. 5; and polyphosphazenes, FIG. 6.

One of the most important criteria is that the biodegradable polymer matrix should be capable of holding a catalyst and swell in 20 weight percent hydrogen peroxide mixture. The peroxide swollen polymer when exposed to elevated temperature (>60 deg C) should decompose the peroxide and yet retain the oxygen released in the resultant foam. Furthermore, the foam should deliver the oxygen when it is sufficiently moistened.

In order to meet the requirements, the synthetic biodegradable polymer matrix should contain at least two polymer segments wherein the first polymer segment provides biodegradability and the second polymer segment provides foam forming ability, as well as augmenting biodegradability. Studying and understanding the structure-property relationship led us to conceptualize the potential candidate polymers listed in Table 1.

TABLE 1

| Backbone Functionality | Polymer Precursor | Commercial Availability | Ionomer Choice (Ionic segments) |
|---|---|---|---|
| Caprolactone | Hydroxyl terminated poly(caprolactone) diols | Yes. Available in different molecular weight and hydroxyl number | Carboxyl (e.g. dimethylol propionic acid, commercially available) |
| Ethylene oxide | Hydroxyl terminated Poly(ethylene oxide) | Yes. Same as above | Sulfonic acid |
| Hydroxy butyric acid (HBA) | Formation of ester diol by reacting HBA and ethylene glycol followed by esterification with diacids | No. Two step process and HBA has limited supply. | Phosphonic acid |
| Lactic acid | Same as above | No. Two step process. Cheaper compared to HBA | |
| Sebacic Acid | Formation of Hydroxyl terminated sebacic acid esters | No. One step process | |
| Aspartic Acid | Poly(aspartic acid) | Yes. Cannot be used as oligomer for polymer formation but could be used to form degradable crosslinking sites | |

The polymer precursors and the ionomers listed above in Table 1 provide the biodegradability and foam foaming ability to the polymer matrix. They could be covalently linked to form a swellable biodegradable polymer matrix in 20% hydrogen peroxide solution. We have used isocyanate precursors to link the segmented biodegradable polymer for proof of principle demonstration. Details of the test plan are provided as follows:

Caprolactone Urethane Work Plan
  A. Category: Thermoplastic or Thermoset
Materials:
Caprolactone diol, FIG. 7, e.g., PERSTORP CAPA 2054, PERSTORP CAPA 2205.
OH Functional prepolymer, FIG. 8, idealized structure example.
NCO prepolymer, FIG. 9.
Caprolactone Triol cross-linker, FIG. 10, e.g. PERSTORP CAPA 3031.
Variables:
  1) Caprolactone Diol molecular weight
    a) CAPA 2054 (550 MW)
      i) 90% of diol wt
      ii) 75% of diol wt
      iii) 50% of diol wt
    b) CAPA 2205 (2000 MW)
      i) 90% of diol wt
      ii) 75% of diol wt
      iii) 50% of diol wt
  2) Loading of Carboxylic acid functional Urethane diol
    i) 10% of diol wt
    ii) 25% of diol wt
    iii) 50% of diol wt
  3) Crosslinker concentration
    a) CAPA 3031 (300 MW)
      i) 5% solids wt
      ii) 10% solids wt
      iii) 15% solids wt
    Other options:
    b) 1,1,1-Tris hydroxymethyl propane (TMP)
    c) Poly(aspartic acid) biodegradable crosslinker Constants:
1) NCO Prepolymer
2) Isocyanate to hydroxyl ratio 1.1/1
3) Solvent NMP
4) Curing Temperature and Humidity Matrix:

| Formulation: | Diol CAPA 2054 | Diol CAPA 2205 | Diol Carboxylic Acid Functional Urethane Diol | Crosslinker Triol CAPA 3031 |
|---|---|---|---|---|
| 1 |  | 90% of diol wt | 10% of diol wt | 5% solids wt |
| 2 |  | 75% of diol wt | 25% of diol wt | 5% solids wt |
| 3 |  | 50% of diol wt | 50% of diol wt | 5% solids wt |
| 4 |  | 90% of diol wt | 10% of diol wt | 10% solids wt |
| 5 |  | 75% of diol wt | 25% of diol wt | 10% solids wt |
| 6 |  | 50% of diol wt | 50% of diol wt | 10% solids wt |
| 7 |  | 90% of diol wt | 10% of diol wt | 15% solids wt |
| 8 |  | 75% of diol wt | 25% of diol wt | 15% solids wt |
| 9 |  | 50% of diol wt | 50% of diol wt | 15% solids wt |
| 10 | 90% of diol wt |  | 10% of diol wt | 5% solids wt |
| 11 | 75% of diol wt |  | 25% of diol wt | 5% solids wt |
| 12 | 50% of diol wt |  | 50% of diol wt | 5% solids wt |
| 13 | 90% of diol wt |  | 10% of diol wt | 10% solids wt |
| 14 | 75% of diol wt |  | 25% of diol wt | 10% solids wt |
| 15 | 50% of diol wt |  | 50% of diol wt | 10% solids wt |
| 16 | 90% of diol wt |  | 10% of diol wt | 15% solids wt |
| 17 | 75% of diol wt |  | 25% of diol wt | 15% solids wt |
| 18 | 50% of diol wt |  | 50% of diol wt | 15% solids wt |

Poly(lactic Acid)Diol Urethane Work Plan
  B. Category: Thermoplastic
Materials:
Poly(lactide diol), FIG. 11.
OH Functional prepolymer, FIG. 8, idealized structure example.
NCO prepolymer, FIG. 9.
Variables:
  1) Poly(Lactide diol)
    i) 90% of diol wt
    ii) 75% of diol wt
    iii) 50% of diol wt
  2) Loading of Carboxylic acid functional Urethane diol
    i) 10% of diol wt
    ii) 25% of diol wt
    iii) 50% of diol wt
Constants:
  1) NCO prepolymer
  2) Isocyanate to hydroxyl ratio
  3) Solvent NMP
  4) Temperature and humidity
Matrix:

| Formulation: | Diols Poly(lactide diol) | Diol Carboxylic Acid Functional Urethane Diol | Crosslinker CAPA 3031 |
|---|---|---|---|
| 1 | 90% of diol wt | 10% of diol wt | 5% solids wt |
| 2 | 75% of diol wt | 25% of diol wt | 5% solids wt |
| 3 | 50% of diol wt | 50% of diol wt | 5% solids wt |
| 4 | 90% of diol wt | 10% of diol wt | 10% solids wt |
| 5 | 75% of diol wt | 25% of diol wt | 10% solids wt |
| 6 | 50% of diol wt | 50% of diol wt | 10% solids wt |
| 7 | 90% of diol wt | 10% of diol wt | 15% solids wt |
| 8 | 75% of diol wt | 25% of diol wt | 15% solids wt |
| 9 | 50% of diol wt | 50% of diol wt | 15% solids wt |

Poly(ethylene glycol)Urethane Work Plan
  C. Category: Thermoplastic or Thermoset
Materials:
Poly(ethylene glycol), FIG. 12, Aldrich 600 MW, Aldrich 2000, MW.
OH Functional prepolymer, FIG. 8, idealized structure example.
NCO prepolymer, FIG. 9.
Caprolactone Triol cross-linker, FIG. 10, e.g. PERSTORP CAPA 3031.
Variables:
  1) Poly(ethylene glycol) molecular weight
    a) PEG (600 MW)
      i) 90% of diol wt
      ii) 75% of diol wt
      iii) 50% of diol wt
    b) PEG (2000 MW)
      i) 90% of diol wt
      ii) 75% of diol wt
      iii) 50% of diol wt
  2) Loading of Carboxylic acid functional Urethane diol
    a) 10% of diol wt
    b) 25% of diol wt
    c) 50% of diol wt
  3) Crosslinker concentration
    a) CAPA 3031 (300 MW)
      i) 5% solids wt
      ii) 10% solids wt
      iii) 15% solids wt
    Other options:
      b) 1,1,1-Tris hydroxymethyl propane (TMP)
      c) Poly (aspartic acid)
Constants:
  1) NCO Prepolymer
  2) Isocyanate to hydroxyl ratio 1.1/1
  3) Solvent NMP
  4) Curing Temperature and Humidity Matrix:

| Formulation: | Diol PEG 600 | Diol PEG 2000 | Diol Carboxylic Acid Functional Urethane Diol | Crosslinker Triol CAPA 3031 |
|---|---|---|---|---|
| 1 | | 90% of diol wt | 10% of diol wt | 5% solids wt |
| 2 | | 75% of diol wt | 25% of diol wt | 5% solids wt |
| 3 | | 50% of diol wt | 50% of diol wt | 5% solids wt |
| 4 | | 90% of diol wt | 10% of diol wt | 10% solids wt |
| 5 | | 75% of diol wt | 25% of diol wt | 10% solids wt |
| 6 | | 50% of diol wt | 50% of diol wt | 10% solids wt |
| 7 | | 90% of diol wt | 10% of diol wt | 15% solids wt |
| 8 | | 75% of diol wt | 25% of diol wt | 15% solids wt |
| 9 | | 50% of diol wt | 50% of diol wt | 15% solids wt |
| 10 | 90% of diol wt | | 10% of diol wt | 5% solids wt |
| 11 | 75% of diol wt | | 25% of diol wt | 5% solids wt |
| 12 | 50% of diol wt | | 50% of diol wt | 5% solids wt |
| 13 | 90% of diol wt | | 10% of diol wt | 10% solids wt |
| 14 | 75% of diol wt | | 25% of diol wt | 10% solids wt |
| 15 | 50% of diol wt | | 50% of diol wt | 10% solids wt |
| 16 | 90% of diol wt | | 10% of diol wt | 15% solids wt |
| 17 | 75% of diol wt | | 25% of diol wt | 15% solids wt |
| 18 | 50% of diol wt | | 50% of diol wt | 15% solids wt |

Bio-degradable Hydrogels from Ring Opening Polymerization

D. Category: Thermoplastic (Ring Opening Polymerization)

Materials:
Trimethylene carbonate(1,3-Dioxan-2-one), FIG. 13.
Caprolactone, FIG. 14.
Hydroxybutyric acid glycerol ester, FIG. 15.

Experimental:
Ring opening polymerization of TMC or CL using Tin(II) 2-ethylhexanoate (catalyzed), with dimethylol propionic acid (DMPA)

Variables:
1) TMC
2) CL
3) DMPA

Constants:
1) Catalyst concentration
2) Solvent
3) Temperature
4) Polymerization time Hydroxybutyric Acid Urethane Work Plan E. Category: Thermoplastic Materials:
Hydroxybutyric acid glycerol ester, FIG. 15.
OH Functional prepolymer, FIG. 8, idealized structure example.
NCO prepolymer, FIG. 9.
Caprolactone Triol cross-linker, FIG. 10, e.g. PERSTORP CAPA 3031.

Variables:
1) Hydroxybutyric acid glycol ester
  i) 90% of diol wt
  ii) 75% of diol wt
  iii) 50% of diol wt
2) Loading of Carboxylic acid functional Urethane diol
  i) 10% of diol wt
  ii) 25% of diol wt
  iii) 50% of diol wt
  iv)

Constants:
1. NCO prepolymer
2. Isocyanate to hydroxyl ratio 1.1/1
3. Solvent NMP
4. Curing temperature and humidity Matrix:

| Formulation: | Diols Poly(lactide diol) | Diol Carboxylic Acid Functional Urethane Diol | Crosslinker CAPA 3031 |
|---|---|---|---|
| 1 | 90% of diol wt | 10% of diol wt | 5% solids wt |
| 2 | 75% of diol wt | 25% of diol wt | 5% solids wt |
| 3 | 50% of diol wt | 50% of diol wt | 5% solids wt |
| 4 | 90% of diol wt | 10% of diol wt | 10% solids wt |
| 5 | 75% of diol wt | 25% of diol wt | 10% solids wt |
| 6 | 50% of diol wt | 50% of diol wt | 10% solids wt |
| 7 | 90% of diol wt | 10% of diol wt | 15% solids wt |
| 8 | 75% of diol wt | 25% of diol wt | 15% solids wt |
| 9 | 50% of diol wt | 50% of diol wt | 15% solids wt |

The caprolactone polyol (CAPA) and acid functionalized prepolymers were mixed with 0.5 wt. % sodium carbonate and reacted with a commercially available isocyanate prepolymer to produce a biodegradable polymer composition (Table 2). The samples were soaked in 20 wt. % hydrogen peroxide and exposed to 50° C. for 2 hours to obtain oxygen containing polymer foams. It was observed that the polymer matrix did not swell in hydrogen peroxide and eventually did not foam. We believe this could be due to the ionomer concentration on the polymer backbone was not sufficient enough to result in a hydrogel matrix. We could mitigate this challenge by either increasing the ionomer concentration or reducing the molecular weight of CAPA segments.

TABLE 2

CAPA polymer composition.

| Sample Reference | Prepolymer | PolyIsocyanate (Tolonate HDT) wt. % |
|---|---|---|
| 53424-16-2 | 50% 550 MW CAPA; 50% Acid Functional Diol | 5% |
| 53424-16-3 | 50% 550 MW CAPA; 50% Acid Functional Diol | 10% |
| 53424-16-4 | 75% 550 MW CAPA; 25% Acid Functional Diol | 5% |

TABLE 2-continued

CAPA polymer composition.

| Sample Reference | Prepolymer | PolyIsocyanate (Tolonate HDT) wt. % |
|---|---|---|
| 53424-16-5 | 75% 550 MW CAPA; 25% Acid Functional Diol | 10% |
| 53424-16-6 | 50% 2,000 MW CAPA; 50% Acid Functional Diol | 5% |
| 53424-16-7 | 50% 2,000 MW CAPA; 50% Acid Functional Diol | 10% |
| 53424-16-8 | 75% 2,000 MW CAPA; 25% Acid Functional Diol | 5% |
| 53424-16-9 | 75% 2,000 MW CAPA; 25% Acid Functional Diol | 10% |

The biodegradation analysis of this polymer matrix was conducted and showed more than 10% weight loss after 10 days (FIG. 2). It was interesting to see the higher ionomer concentration enhanced the rate of biodegradability. This increase in ionomer concentration increased the number of hydration sites that made the environment more conducive for biodegradation. The increase of CAPA molecular weight had no effect on the rate of biodegradation. One might expect the higher molecular weight would have more hydrolyzing repeat units per mole and therefore result in higher biodegradability compared to a low molecular weight CAPA segment. We believe the crosslink density of the polymer matrix was high enough to offset these molecular weight effects.

Polymer Matrix Derived From Polyethylene Glycol and Acid Functionalized Prepolymer The biodegradable polymer containing the polyethylene glycol (PEG) segments was synthesized according to the scheme illustrated in FIG. 3. The details of the synthesis and characterization of this polymer matrix are:

(1) 50% PEG (2000 MW)/50% Acid Functional Precursor

In a 500 mL round bottom flask fitted with a thermocouple, a water cooled condenser, overhead stirrer, argon inlet for purge, a heating mantle, and fitted with an addition funnel, charge carboxylic acid urethane diol 53424-6-10 (20.4 grams), and polyethylene glycol diol (10.00 grams) then rinse it in with Methyl Ethyl Ketone (23.4 grams). Heat the mixture gently to 60° C., under argon purge, while mixing. Rinse Dibutyl tin dilaurate (0.0102 grams) into the reactor. Fill the addition funnel with Isophorone diisocyanate "IPDI" (3.10 grams). Then begin drop wise addition of the IPDI and control the addition to finish about 1 hour later.

(2) 75% PEG (2000 MW)/25% Acid Functional Precursor

In a 500 mL round bottom flask fitted with a thermocouple, a water cooled condenser, overhead stirrer, argon inlet for purge, a heating mantle, and fitted with an addition funnel, charge carboxylic acid urethane diol 53424-6-10 (20.60 grams), and polyethylene glycol diol (30.00 grams) then rinse it in with Methyl Ethyl Ketone (44.50 grams). Heat the mixture gently to 60° C., under argon purge, while mixing. Rinse Dibutyl tin dilaurate (0.0048 grams) into the reactor. Fill the addition funnel with Isophorone diisocyanate "IPDI" (5.10 grams). Then begin drop wise addition of the IPDI and control the addition to finish about 1 hour later.

(3) 50% PEG (600W)/50% Acid Functional Precursor

In a 500 mL round bottom flask fitted with a thermocouple, a water cooled condenser, overhead stirrer, argon inlet for purge, a heating mantle, and fitted with an addition funnel, charge carboxylic acid urethane diol 53424-6-10 (20.40 grams), and polyethylene glycol diol (10.01 grams) then rinse it in with Methyl Ethyl Ketone (27.1 grams). Heat the mixture gently to 60° C., under argon purge, while mixing. Rinse Dibutyl tin dilaurate (0.0069 grams) into the reactor. Fill the addition funnel with Isophorone diisocyanate "IPDI" (7.30 grams). Then begin drop wise addition of the IPDI and control the addition to finish about 1 hour later.

(4) 75% PEG (600W)/25% Acid Functional Precursor

In a 500 mL round bottom flask fitted with a thermocouple, a water cooled condenser, overhead stirrer, argon inlet for purge, a heating mantle, and fitted with an addition funnel, charge carboxylic acid urethane diol 53424-6-10 (20.50 grams), and polyethylene glycol diol (10.21 grams) then rinse it in with Methyl Ethyl Ketone (30.35 grams). Heat the mixture gently to 60° C., under argon purge, while mixing. Rinse Dibutyl tin dilaurate (0.0101 grams) into the reactor. Fill the addition funnel with Isophorone diisocyanate "IPDI" (10 grams). Then begin drop wise addition of the IPDI and control the addition to finish about 1 hour later.

(5) Peroxide Swelling Procedure
1) Weigh each sample
2) Prepare 20% hydrogen peroxide solution by diluting 30% with distilled water
3) Pour enough hydrogen peroxide into a beaker so that the sample is submerged
4) Remove the sample at intervals, blot dry and record the weight
5) Calculate the percent hydration The polyethylene glycol based urethanes hydrated faster than the CAPA urethanes. There was a distinct trend of increasing hydration rate with PEG molecular weight and decreased crosslinker concentration.

(6) Dimensional Change with Swelling Procedure
1) Cut each sample with a ¾ inch diameter round sample punch
2) Prepare 20% hydrogen peroxide solution by diluting 30% with distilled water
3) Pour enough hydrogen peroxide into a beaker so that the sample is submerged
4) Remove the sample at intervals, blot dry and record the diameter
5) Calculate the swelling % change The final dimensional increase was compared to the two hour hydration percent for a number of PEG based samples. The samples that hydrate the most will swell the most in peroxide. This is understandable and helps to validate the hydration data.

The PEG diol and acid functionalized prepolymers were mixed with 0.5 wt. % sodium carbonate and reacted with isocyanate prepolymer to produce biodegradable polymer composition. The polymer matrix obtained had significant swelling (Table 3) and the hydration rate increased with the increasing molecular weight of PEG segment. Since these polymers had a high hydration rate, their mechanical properties in the hydrogel state were inadequate. We believe this could be easily improved by optimizing the hydrophilic character of the polymers and increasing the crosslink density of the polymer. The swollen polymer on exposure to heat did not foam. This was surprising as we expected the sodium carbonate present in the swollen polymer matrix would decompose hydrogen peroxide at elevated temperature and release oxygen which would result in the foaming of the polymer matrix.

We speculate that either the acid based ionomer might have neutralized the catalyst (sodium carbonate) that is necessary to decompose hydrogen peroxide to form oxygen or the isocyanate precursor might have reacted with the carbonates. In order to validate our hypothesis, the sodium carbonate concentration in the resultant polymer matrix was analyzed and compared with initial theoretical loading of sodium carbonate as follows:

Titration of Sodium Carbonate

In order to gauge any interference of the sodium carbonate with residual isocyanate in the urethane, titrations were performed. CAPA-PEG hybrid urethane with 1% crosslinker was formulated with 9.09% sodium carbonate. The sample was cured and cut into pieces of known mass. These pieces, as well as neat sodium carbonate powder, were titrated against HCl to neutralize the sodium carbonate. The method consists of weighing a sample approx. 3-4 g into an Erlenmeyer flask equipped with a magnetic stirrer, and dissolve in 30 mL toluene; close the flask and set on the magnetic stirrer for 10 min so reaction can proceed. Charge 20 mL of Methanol and titrate with HCl to reach a pH of 4. Repeat in triplicate and average the results. The standard deviations overlap, thus suggesting that there is no interference of the isocyanate with the catalyst.

Titrino Autotitrator
  Titrant: HCl=1 mol/L in methanol
  Solvents: Toluene and methanol
  Magnetic Swing-out Stirrer
  Exchange units
  Solvotrode Electrode
Method: Reference MetroOhm application bulletin No. 200/2 e We could not, however, find any convincing evidence for sodium carbonate neutralization with the acid containing ionomer nor by reacting with the isocyanate prepolymer.

Details of Synthesis and Characterization of Polymer Matrix Derived From CAPA and PEG Segments PEG Based Hydroxyl Precursor (PEG-IPDI-PEG)

53424-43-34 Method:

In a 250 mL roundbottom flask fitted with a thermocouple, a water cooled condenser, overhead stirrer, argon inlet for purge, a heating mantle, and fitted with an addition funnel, charge Poly(ethylene glycol) (2,000 MW 75.00 grams) rinse it in with methyl ethyl ketone "MEK" (65.00 grams), Dibutyl tin Dilaurate (0.0898 grams) then rinse in with MEK (5.36 grams). Heat the mixture gently to 60° C., under argon purge, while mixing, until the solids dissolve. Fill the addition funnel with Isophorone diisocyanate "IPDI" (40.4 grams). Then begin drop wise addition of the IPDI and finish the addition after 1 hour. Rinse in with more MEK (25.02 grams). Allow the reaction to mix at 60° C. for another hour. Shut off heater, and cool to room temperature while mixing overnight.

CAPA Based Isocyanate Precursor (IPDI-CAPA-IPDI)

53424-42-34 Method:

In a 250 mL roundbottom flask fitted with a thermocouple, a water cooled condenser, overhead stirrer, argon inlet for purge, a heating mantle, and fitted with an addition funnel, charge Caprolactone Diol (550 MW 50.24 grams), Dibutyl tin Dilaurate (0.0931 grams) then rinse it in with methyl ethyl ketone "MEK" (65 grams). Heat the mixture gently to 60° C., under argon purge, while mixing, until the solids dissolve. Fill the addition funnel with Isophorone

TABLE 3

Degree of swelling (or nominal hydration) of polymer matrix derived from polyethylene glycol and acid functionalized prepolymer.

| Sample Reference | 53424-18 600 MW PEG 50/50 (PEG/pre) | 53424-19 600 MW PEG 75/25 (PEG/pre) | 53424-20 2000 MW PEG 50/50 (PEG/pre) | 53424-21 2000 MW PEG 75/25 (PEG/pre) | Tolonate HDT (PolyNCO) | Nominal Hydration (%) at specified time intervals | | |
|---|---|---|---|---|---|---|---|---|
| | | | | | | 20 min | 60 min | 120 min |
| 53424-22-1 | x | | | | (5%) | 11 | 21 | 28 |
| 53424-22-2 | x | | | | (10%) | 14 | 25 | 28 |
| 53424-22-4 | | x | | | (10%) | 55 | 72 | 71 |
| 53424-22-5 | | | x | | (5%) | 52 | 81 | 93 |
| 53424-22-6 | | | x | | (10%) | 47 | 59 | 65 |
| 53424-22-7 | | | | x | (5%) | 80 | 152 | 213 |

The PEG based polymer showed approximately 20% weight reductions after 10 days. As seen in the CAPA based polymer, the rate of biodegradability of the PEG based polymer increased with higher hydrophilic concentration of the PEG segments. Overall the PEG based polymer showed a higher rate of biodegradation compared to the CAPA based polymer.

Polymer Matrix Derived From Caprolactone Polyol and Polyethylene Glycol

Segmented copolymers containing CAPA and PEG segments are unique and not commercially available. In order to form a polymer matrix with both CAPA and PEG segments, CAPA based isocyanate precursors and PEG based hydroxyl precursors were individually synthesized and reacted together to form a segmented biodegradable matrix. A representative formulation is provided in Table 4. The details of the synthesis are as follows:

diisocyanate "IPDI" (40.4 grams). Then begin drop wise addition of the IPDI and finish the addition after 1 hour. Rinse in with more MEK (25.02 grams). Allow the reaction to mix at 60° C. for another hour. Shut off heater, and cool to room temperature while mixing overnight.

CAPA PEG Hybrid Urethane Formulation 53424-74-20 Method:

In a 1 L reactor fitted with a thermocouple, a water cooled condenser, overhead stirrer, argon inlet for purge, a heating mantle, and fitted with an addition funnel, charge CAPA based Isocyanate Precursor (200.05 grams), Dibutyl tin Dilaurate (0.51 grams) then rinse it in with methyl ethyl ketone "MEK" (251.76 grams). Charge in PEG Based Hydroxyl Precursor (299.95 grams) and rinse in with MEK (255.37 grams). Heat the mixture gently to 60° C., under argon purge, while mixing. Allow the reaction to mix at 60° C. for 1 hour. Shut off heater, and cool to room temperature while mixing overnight. The solution will be very viscous. Charge in Tolonate HDT (2.5 grams), followed by more MEK (102.02 grams). Formulate as needed with catalyst.

Peroxide Swelling Procedure
1) Weigh each sample
2) Prepare 20% hydrogen peroxide solution by diluting 30% with distilled water
3) Pour enough hydrogen peroxide into a beaker so that the sample is submerged
4) Remove the sample at intervals, blot dry and record the weight
5) Calculate the percent hydration Hydration Time Correlation to CAPA/PEG Hybrid Formulation A series of CAPA/PEG hybrid formulations were prepared at different ratios of isocyanate and hydroxyl precursor weight ratios; specifically at ratios of 20/80, 40/60, and 60/40. These formulations correspond to isocyanate/hydroxyl equivalent ratios. Their time to 50% hydration was calculated, and compared to their respective isocyanate to hydroxyl equivalent ratio. The trend observed suggests that the more polyethylene glycol in the formulation, the faster it hydrates.

TABLE 4

Polymer matrix formulations based on CAPA and PEG segments.

| Sample Ref. | Prepolymer [1] | Polyisocanate (Tolonate HDT) wt. % [2] | Sodium Carbonate wt. % [3] |
|---|---|---|---|
| 53424-56-13 | 40% 550 MW CAPA; 60% 2000 MW PEG Diol | 3 | 2 |
| 53424-56-24 | 40% 550 MW CAPA; 60% 2000 MW PEG Diol | 1 | 2 |

[1] Prepolymers were synthesized by reacting specified diols with isophorone diisocyanate at NCO/OH ratio of 2:1 for CAPA and 0.5:1 for PEG
[2] Polyisocyanate was added based on prepolymer solids.
[3] Sodium carbonate was added based on total solids and it was ground and sieved to less than 53 microns before mixing.

The polymer matrix based on CAPA and PEG did swell in 20% hydrogen peroxide solution and showed good foam forming ability after thermal exposure. Oxygen analysis of these foams and the results are reported in Table 5.

TABLE 5

Oxygen concentration results of polymer matrix derived from CAPA and PEG segments.

| Lot ID | Total $O_2$ Delivery 24 hour (ppm) |
|---|---|
| 53424-56-13 | 25.3 |
| 53424-56-24 | 25.1 |
| 53424-66-22 | 24.4 |

It was observed that the total oxygen delivery was only 25 ppm over a period of 24 hours. It was speculated that the foam samples may have open cells and therefore did not retain enough oxygen in the matrix. In order to investigate the morphology of the foam samples, SEM investigation was performed. The experimental biodegradable foam samples have a discrete structure with no evidence of expanded foam structure.

Polymer Matrix Formulated with Additives for Making Closed Cell Polymer Foam

This more openness in the foam structure is possibly due to one or both of the following factors:

(a) Higher foam rigidity or lack of foam coalescence
(b) Rate of decomposition of peroxide is much faster than foam relaxation The following technical approaches were attempted to address the above challenges:

(a) Approach 1: Use of Guar Gum

Guar gum is a natural polymer adhesive. Incorporating Guar gum in the formulation is expected to lower the foam rigidity and enhance foam coalescence. It was incorporated directly into the polymer matrix at various levels and was also first coated onto sodium carbonate (encapsulating sodium carbonate with the additives first) followed by dispersing them into the polymer matrix. The formulations obtained from this approach are provided in Table 6 and the experimental details are as follows:

Details of Polymer Matrix Formulated with Alternative Catalysts to Make Closed Cell Polymer Foam CAPA-PEG Hybrid with 50/50 Guar Gum Take sodium carbonate (10.0 grams) and dissolve into distilled water (50 grams). After dissolving charge Hercules Supercol U Guar Gum (10.0 grams). Mix vigorously to hydrate thoroughly. The mixture will form a thick paste within a minute, and continue mixing until the consistency is uniform. Let it sit for a half hour to allow any clumps to hydrate evenly. Place in a vacuum oven 60° C. overnight to obtain dry solids. Grind the solids the next day with mortar and pestle and sieve to less than 106 μm.

Take 59.93 grams of 53424-74-10 (40% 550 MW CAPA; 60% 2000 MW PEG Diol) and mix in 0.503 grams of 50/50 Guar Gum. Cast into a 5×5 Teflon mold and air dry. Note: this appeared to gel faster than the urethane alone.

CAPA-PEG Hybrid with 67/33 Guar Gum

Take sodium carbonate (10.0 grams) and dissolve into distilled water (50 grams). After dissolving, charge Hercules Supercol U Guar Gum (5.0 grams). Mix vigorously to hydrate thoroughly. The mixture will form a thick paste within a minute, and continue mixing until the consistency is uniform. Let it sit for a half hour to allow any clumps to hydrate evenly. Place in a vacuum oven 60° C. overnight to obtain dry solids. Grind the solids the next day with mortar and pestle and sieve to less than 106 μm.

Take 60.02 grams of 53424-74-10 (40% 550 MW CAPA; 60% 2000 MW PEG Diol) and mix in 0.377 grams of 567/33 Guar Gum. Cast into a 5×5 Teflon mold and air dry.

Peroxide Swelling Procedure

1) Weigh each sample
2) Prepare 20% hydrogen peroxide solution by diluting 30% with distilled water
3) Pour enough hydrogen peroxide into a beaker so that the sample is submerged
4) Remove the sample at intervals, blot dry and record the weight
5) Calculate the percent hydration

TABLE 6

Formulations based on guar gum.

| Sample Ref. | Comments |
|---|---|
| 53424-78-25 | Control |
| 53424-80-10 | Mixed Guar gum with catalyst (50/50 wt. %) |
| 53424-80-20 | Mixed Guar gum with catalyst (33/67 wt. %) |
| 53424-81-11 | Mixed Guar gum with catalyst (50/50 wt. %) and placed the catalyst in between two PU films |
| 53424-81-20 | Mixed Guar gum with catalyst (33/67 wt. %) and placed the catalyst in between two PU films |

Catalyst used was sodium carbonate 2 wt. % based on prepolymer solids

Crosslinker used was Tolonate HDT 1 wt. % based on prepolymer solids

Prepolymer comprised of 40% 550 MW CAPA; 60% 2,000 MW PEG Diol (b) Approach 2: Replacement for Sodium Carbonate to Control the Rate of Peroxide Decomposition in the Foam Matrix For this purpose, two alternate catalysts were chosen: (a) Silver and (b) PVP-iodine complex. The reason for choosing these catalysts was due to the fact that they decompose hydrogen peroxide an order of magnitude slower compared to sodium carbonate. Furthermore, both silver and iodine have antiseptic properties and would provide additional benefits to the end user. The formulations obtained from this approach are provided in Table 7 and the experimental details are as follows:

50/50 Encapsulation of PVP-I2

Take PVP-Iodine Complex (3.17 grams) and dissolve into distilled water (20 grams). After dissolving, charge Hercules Supercol U Guar Gum (3.22 grams). Mix vigorously to dissolve. Place in a vacuum oven 60° C. overnight to obtain dry solids. Grind the solids the next day with mortar and pestle and sieve to less than 106 μm.

CAPA-PEG Hybrid with Silver Zeolite

Grind the granular silver zeolite (Aldrich 382280) with a mortar and pestle, then sieve with a 106 μm screen.

Take 59.90 grams of 53424-44-10(40% 550 MW CAPA; 60% 2000 MW PEG Diol) and 0.507 grams of the <106 μm zeolite. Mix well and cast into a 5×5inch Teflon mold. Allow it to air dry.

Peroxide Swelling Procedure
1) Weigh each sample
2) Prepare 20% hydrogen peroxide solution by diluting 30% with distilled water
3) Pour enough hydrogen peroxide into a beaker so that the sample is submerged
4) Remove the sample at intervals, blot dry and record the weight
5) Calculate the percent hydration

TABLE 7

Formulations based on alternative peroxide decomposition catalyst.

| Sample Ref. | Comments |
|---|---|
| 53424-89-6 | PVP-Iodine complex (50/50 wt. % with Guar gum) |
| 53424-89-31 | PVP-Iodine complex (50/50 wt. % with Guar gum) <106 μm particle reduction |
| 53424-89-21 | Silver exchanged Zeolite |

Prepolymer comprises of 40% 550 MW CAPA; 60% 2,000 MW PEG Diol

Crosslinker used was Tolonate HDT 1 wt. % based on prepolymer solids

Catalyst used was 2 wt. % based on prepolymer solids

It was observed that the samples based on guar gum when soaked in 20% hydrogen peroxide solution had a very tacky surface and could not be removed from the mesh sheet. This observation supports the assessment that guar gum would form a less rigid foam and would assist in the coalescence of the foam.

Polymer matrix formulated with PVP-iodine catalysts swelled in 20% hydrogen peroxide solution. However, it was observed that the matrix had uneven texture and after foaming, the test specimen was hard and brittle.

The polymer matrix with silver based catalyst did not foam the matrix. When samples were soaked in peroxide solution, a froth was noted and the pH of the peroxide medium increased. The silver catalyst used was based on supported zeolites (sodium aluminum silicate) and we speculate the catalyst support was not completely neutralized. The residual base (such as sodium hydroxide) would have initiated the peroxide decomposition during the soak time. It is clear from our studies the rate of peroxide decomposition is critical and a key factor for producing foam with the desired closed cell morphology.

The foam samples from the above two approaches were cross sectioned and investigated under SEM. The foam samples containing guar gum had closed cell morphology with very limited defects. The oxygen concentration of these samples was found to be only 20-25 ppm (Table 8). This was a surprising result as this closed cell morphology was expected to hold more gas compared to the open cell structure.

If we believe our earlier samples with open cell architecture have an oxygen concentration of about 25 ppm, then one would expect a higher oxygen concentration from the guar gum formulations that resulted in more closed cell structure. In order to verify, the oxygen permeability (oxygen holding capacity) of the neat polymer matrix cast films, from the formulation comprised of 40% 550 MW CAPA prepolymer and 60% 2,000 MW PEG diol were analyzed.

TABLE 8

Oxygen concentration results for the polymer matrix formulated with additives.

| Sample Reference Description | Total $O_2$ Delivery 24 hr |
|---|---|
| Control | 22.1 |
| Mixed Guar gum with catalyst (50/50 wt. %) | 22.7 |
| Mixed Guar gum with catalyst (33/67 wt. %) | 24.2 |
| Mixed Guar gum with catalyst (50/50 wt. %) and placed the catalyst in between two PU films | 24.0 |
| Mixed Guar gum with catalyst (33/67 wt. %) and placed the catalyst in between two PU films | 23.8 |
| PVP-Iodine complex (50/50 wt. % with Guar gum) | 21.9 |
| PVP-Iodine complex (50/50 wt. % with Guar gum) <106 μm particle reduction | 22.2 |

We have demonstrated the feasibility of making a biodegradable foam. The top candidate based on covalently linked segments of polycaprolactone and polyethylene glycol met the performance requirements for biodegradability, biocompatibility, and foam forming ability.

While the disclosure has been described in detail with respect to specific embodiments thereof, it will be apparent to those skilled in the art that various alterations, modifications and other changes may be made to the disclosure without departing from the spirit and scope of the present disclosure. It is therefore intended that the claims cover all such modifications, alterations and other changes encompassed by the appended claims.

What is claimed is:

1. A foamable composition comprising a prepolymer comprising covalently linked segments of polycaprolactone and polyethylene glycol, a cross-linking agent connecting the polycaprolactone and the polyethylene glycol; a peroxide solution containing 20 wt. % peroxide; and a peroxide decomposition catalyst; wherein the cross-linking agent comprises an isocyanate prepolymer or a cross-linker with isocyanate content between 0.01 wt. % and 40 wt. % and an acid value between 0.01 mg and 100 mg of KOH/g of sample, wherein the cross-linking agent is present in an amount of between 1 wt. % and 3 wt. % based on the amount of prepolymer comprising covalently linked segments of polycaprolactone and polyethylene glycol, wherein the composition is capable of forming a foam that delivers 24.4 to 25.3 parts per million of oxygen within 24 hours.

2. The foamable composition of claim 1, wherein the polycaprolactone is biodegradable with a weight loss of greater than 10 wt. % in 10 days, without the release of toxic products from the biodegradation.

3. The foamable composition of claim 1, wherein a polymer matrix formed from the covalently linked segments of polycaprolactone and polyethylene glycol exhibits greater than or equal to 20 percent nominal hydration exposed to the peroxide solution.

4. The foamable composition of claim 1, wherein the peroxide in the peroxide solution is hydrogen peroxide.

5. The foamable composition of claim 1, wherein the peroxide decomposition catalyst is selected from the group consisting of sodium carbonate, magnesium carbonate, manganese and silver.

* * * * *